United States Patent
Tao et al.

(10) Patent No.: US 11,238,289 B1
(45) Date of Patent: Feb. 1, 2022

(54) AUTOMATIC LIE DETECTION METHOD AND APPARATUS FOR INTERACTIVE SCENARIOS, DEVICE AND MEDIUM

(71) Applicant: Institute of Automation, Chinese Academy of Sciences, Beijing (CN)

(72) Inventors: Jianhua Tao, Beijing (CN); Zheng Lian, Beijing (CN); Bin Liu, Beijing (CN); Licai Sun, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/389,364

(22) Filed: Jul. 30, 2021

(30) Foreign Application Priority Data

Jan. 4, 2021 (CN) .......................... 202110001077.0

(51) Int. Cl.
*G06K 9/00* (2006.01)
*G06N 3/04* (2006.01)
(Continued)

(52) U.S. Cl.
CPC .......... *G06K 9/00765* (2013.01); *A61B 5/164* (2013.01); *G06F 16/7834* (2019.01);
(Continued)

(58) Field of Classification Search
CPC .......... G06K 9/00302; G06K 9/00315; G06K 9/00744; G06K 9/00765; G06F 16/7834; G06F 16/7844; G06N 3/04; A61B 5/164
(Continued)

(56) References Cited

U.S. PATENT DOCUMENTS

| 11,151,385 B2 * | 10/2021 | Iyer | G06K 9/00744 |
| 2020/0065394 A1 * | 2/2020 | Calderon | G06K 9/6267 |
| 2021/0248511 A1 * | 8/2021 | Nadimpalli | G06K 9/46 |

FOREIGN PATENT DOCUMENTS

| CN | 108520753 A | 9/2018 |
| CN | 109793526 A | 5/2019 |

(Continued)

OTHER PUBLICATIONS

Chhaya, et al. (DialogueGCN: A Graph Convolutional Neural Network for Emotion Recognition in Conversation), pp. 1-11. (Year: 2019).*

(Continued)

*Primary Examiner* — Daniel G Mariam
(74) *Attorney, Agent, or Firm* — Bayramoglu Law Offices LLC (57) ABSTRACT

An automatic lie detection method and apparatus for interactive scenarios, a device and a medium to improve the accuracy of automatic lie detection are provided. The method includes: segmenting three modalities, namely a video, an audio and a text, of a to-be-detected sample; extracting short-term features of the three modalities; integrating the short-term features of the three modalities in the to-be-detected sample to obtain long-term features of the three modalities corresponding to each dialogue; integrating the long-term features of the three modalities by a self-attention mechanism to obtain a multi-modal feature of the each dialogue; integrating the multi-modal feature of the each dialogue with interactive information by a graph neutral network to obtain a multi-modal feature integrated with the interactive information; and predicting a lie level of the each dialogue according to the multi-modal feature integrated with the interactive information.

10 Claims, 2 Drawing Sheets

(51) Int. Cl.
    *G06F 16/783*    (2019.01)
    *A61B 5/16*    (2006.01)

(52) U.S. Cl.
    CPC ..... *G06F 16/7844* (2019.01); *G06K 9/00315* (2013.01); *G06K 9/00744* (2013.01); *G06N 3/04* (2013.01)

(58) Field of Classification Search
    USPC ........................................ 382/103, 173, 284
    See application file for complete search history.

(56) References Cited

FOREIGN PATENT DOCUMENTS

| | | |
|---|---|---|
| CN | 110222331 A | 9/2019 |
| CN | 110427803 A | 11/2019 |
| CN | 110969106 A | 4/2020 |
| CN | 112017671 A | 12/2020 |

OTHER PUBLICATIONS

Zheng Lian, et al., Conversational Emotion Analysis via Attention Mechanisms, 2019, pp. 1-5.

Licai Sun, et al., Multi-modal Continuous Dimensional Emotion Recognition Using Recurrent Neural Network and Self-Attention Mechanism, MuSe '20, 2020, pp. 27-34.

\* cited by examiner

AUTOMATIC LIE DETECTION METHOD AND APPARATUS FOR INTERACTIVE SCENARIOS, DEVICE AND MEDIUM

CROSS REFERENCE TO THE RELATED APPLICATIONS

This application is based upon and claims priority to Chinese Patent Application No. 202110001077.0 filed on Jan. 4, 2021, the entire contents of which are incorporated herein by reference.

TECHNICAL FIELD

The embodiments of the application relate to the technical field of lie analysis, in particular to an automatic lie detection method and apparatus for interactive scenarios, a device and a medium.

BACKGROUND

The automatic lie detection technique puts forward a corresponding model and method by summarizing the rule of changes of facial expressions, speeches and texts of people under a lying condition and a non-lying condition to establish a machine with a capacity to capture lie clues, and is able to assist police officers in accelerating interrogations and improving the interrogation efficiency. Existing automatic lie detection methods determine whether a speaker lies by analyzing the facial expressions and speeches of the speaker when the speaker speaks each word.

The existing technique has the following problems: when a testee speaks, only the facial expression and speech of the current word spoken by the testee are analyzed, and the facial expressions and speeches of the testee are not considered in combination, which neglects the influence of the previous lie state of the testee on the current lie state and also neglects interactive information between the testee and people who talk with the testee, thus making detection results inaccurate.

SUMMARY

The embodiments of the application provide an automatic lie detection method and apparatus for interactive scenarios, a device and a medium to improve the accuracy of automatic lie detection.

In a first aspect, the embodiments of the application provide an automatic lie detection method for interaction scenarios, comprising:

inputting a to-be-detected sample;

segmenting a video, an audio and a text of the to-be-detected sample according to preset time periods to obtain video information, audio information and text information in multiple time periods;

extracting short-term video features, short-term audio features and short-term text features in the multiple time periods according to the video information, the audio information and the text information in the multiple time periods;

aggregating all short-term video features, short-term audio features and short-term text features in each dialogue in the to-be-detected sample in chronological order to obtain long-term video features, long-term audio features and long-term text features;

integrating the long-term video features, the long-term audio features and the long-term text features by a multi-modal attention integration strategy to obtain a multi-modal feature of each dialogue in the to-be-detected sample;

inputting the multi-modal feature of each dialogue and speaker information corresponding to each dialogue to a graph neural network in chronological order to obtain a multi-modal feature integrated with interactive information, wherein the speaker information is recognized by means of a pre-trained character information recognition network; and predicting a lie level of each dialogue according to the multi-modal feature integrated with the interactive information.

optionally, segmenting a video, an audio and a text of the to-be-detected sample according to preset time periods to obtain video information, audio information and text information in multiple time periods comprises:

segmenting the video of the to-be-detected sample in seconds, taking all image frames, appearing within one second, in the to-be-detected sample as video information in one time period, and normalizing all the image frames in the video information to obtain images of a first preset size;

segmenting the audio of the to-be-detected sample in seconds, and taking all audio sampling points, appearing within one second, in the to-be-detected sample as audio information in one time period; and segmenting the text of the to-be-detected sample in seconds, and taking words, spoken by a speaker within one second, in the to-be-detected sample as text information in one time period.

Optionally, extracting short-term video features, short-term audio features and short-term text features in the multiple time periods according to the video information, the audio information and the text information in the multiple time periods comprises:

extracting face region images from the short-term video information in the multiple time periods;

correcting and normalizing the face region images to obtain standard facial images of a second preset size;

extracting, by a pre-trained facial expression recognition network, hidden-layer feature representations from the standard facial images to obtain standard facial features;

performing feature statistics on the standard facial features to obtain standard facial features in one time period, and taking the standard facial features as the short-term video features;

obtaining, by calculation, rhythm features, tone features, spectrum parameter features and statistics thereof in the audio information in the multiple time periods, and taking the rhythm features, the tone features, the spectrum parameter features and the statistics thereof as the short-term video features; and obtaining, by calculation, word vectors and statistics thereof in the text information in the multiple time periods, and taking the word vectors and the statistics thereof as the short-term text features.

Optionally, aggregating all short-term video features, short-term audio features and short-term text features in each dialogue in the to-be-detected sample in chronological order to obtain long-term video features, long-term audio features and long-term text features comprises:

extracting all short-term video features in each dialogue in the to-be-detected sample, and calculating all the short-term video features in each dialogue in the to-be-detected sample by a self-attention mechanism to obtain the long-term video features of each dialogue in the to-be-detected sample;

extracting all short-term audio features in each dialogue in the to-be-detected sample, and calculating all the short-term audio features in each dialogue in the to-be-detected sample by the self-attention mechanism to obtain the long-term audio features of each dialogue in the to-be-detected sample; and extracting all short-term text features in each dialogue in the to-be-detected sample, and calculating all the short-term text features in each dialogue in the to-be-detected sample by the self-attention mechanism to obtain the long-term text features of each dialogue in the to-be-detected sample.

Optionally, integrating the long-term video features, the long-term audio features and the long-term text features by a multi-modal attention integration strategy to obtain a multi-modal feature of each dialogue in the to-be-detected sample comprises:

stitching the long-term video features, the long-term audio features and the long-term text features to obtain multi-modal stitched features; and calculating an attention weight of each modality, and integrating the multi-modal stitched features according to the attention weight to obtain the multi-modal feature of each dialogue in the to-be-detected sample, wherein each modality is a video, an audio or a text.

Optionally, inputting the multi-modal feature of each dialogue and speaker information corresponding to each dialogue to a graph neural network in chronological order to obtain a multi-modal feature integrated with interactive information comprises:

taking the multi-modal feature of each dialogue as a feature representation of each sentence node in the graph neural network, and taking the speaker information corresponding to each dialogue as a feature representation of each speaker in the graph neural network;

connecting each sentence node in the graph neural network and a neighborhood sentence of the sentence node by means of an edge, and establishing a sequential relationship model of all sentences in the to-be-detected sample to obtain a sequential relationship of the dialogues in the to-be-detected sample, wherein the edges for connecting the sentences nodes include forward edges and backward edges, a time sequence of a node where each forward edge starts is earlier, a time sequence of a node to which each forward edge points is later, a time sequence of a node where each backward edge starts is earlier, and a time sequence of a node to which each backward edge points is later;

connecting each sentence node in the graph neutral network and a speaker node corresponding to the sentence node by means of an edge, and establishing a speaker information model of each dialogue in the to-be-detected sample to obtain a relationship between each dialogue in the to-be-detected sample and the corresponding speaker; and integrating the multi-modal feature of each dialogue, the sequential relationship, and the relationship between each dialogue and the corresponding speaker to obtain the multi-modal feature integrated with the interactive information.

Optionally, extracting all short-term video features in each dialogue in the to-be-detected sample, and calculating all the short-term video features in each dialogue in the to-be-detected sample by a self-attention mechanism to obtain the long-term video features of each dialogue in the to-be-detected sample comprises:

assigning the short-term video features in each dialogue in the to-be-detected sample to three variables, performing m times of linear mapping on the three variables, and recording three variables obtained after each time of mapping from the first time of mapping to the mth times of mapping;

calculating attention weights of the three variables obtained after each time of mapping, and calculating a weight sum according to the attention weights obtained by calculation to obtain a short-term video feature after each time of mapping;

sequentially stitching the short-term video features obtained after each time of mapping to obtain short-term video features integrated with sequential information; and calculating attention weights of the short-term video features integrated with the sequential information, and calculating a weight sum of the short-term video features integrated with the sequential information according to the attention weights obtained by calculation to obtain the long-term video feature of each dialogue in the to-be-detected sample, wherein the long-term video features and the long-term text features are calculated in a same way as the long-term video features.

In a second aspect, the embodiments of the application provide an automatic lie detection apparatus for interactive scenarios, comprising:

a sample input module used for inputting a to-be-detected sample;

a sample segmenting module used for segmenting a video, an audio and a text of the to-be-detected sample according to preset time periods to obtain video information, audio information and text information in multiple time periods;

a short-term feature extraction module used for extracting short-term video features, short-term audio features and short-term text features in the multiple time periods according to the video information, the audio information and the text information in the multiple time periods;

a long-term feature extraction module used for aggregating all short-term video features, short-term audio features and short-term text features in each dialogue in the to-be-detected sample in chronological order to obtain long-term video features, long-term audio features and long-term text features;

a multi-modal integration module used for integrating the long-term video features, the long-term audio features and the long-term text features by a multi-modal attention integration strategy to obtain a multi-modal feature of each dialogue in the to-be-detected sample;

an interactive modeling module used for inputting the multi-modal feature of each dialogue and speaker information corresponding to each dialogue to a graph neural network in chronological order to obtain a multi-modal feature integrated with interactive information, wherein the speaker information is recognized by means of a pre-trained character information recognition network; and a lie level prediction module used for predicting a lie level of each dialogue according to the multi-modal feature integrated with the interactive information.

Optionally, the sample segmenting module comprises:

a video segmenting sub-module used for segmenting the video of the to-be-detected sample in seconds, taking all image frames, appearing within one second, in the to-be-detected sample as video information in one time period, and normalizing all the image frames in the video information to obtain images of a first preset size;

an audio segmenting sub-module used for segmenting the audio of the to-be-detected sample in seconds, and taking all audio sampling points, appearing within one second, in the to-be-detected sample as audio information in one time period;

a text segmenting sub-module used for segmenting the text of the to-be-detected sample in seconds, and taking words, spoken by a speaker within one second, in the to-be-detected sample as text information in one time period.

Optionally, the short-term feature extraction module comprises:

a first image extraction sub-module used for extracting face region images from the short-term video information in the multiple time periods;

a first image processing sub-module used for correcting and normalizing the face region images to obtain standard facial images of a second preset size;

a facial expression recognition sub-module used for extracting, by a pre-trained facial expression recognition, hidden-layer feature representations from the standard facial images to obtain standard facial features;

a short-term video feature extraction sub-module used for performing feature statistics on the standard facial features to obtain standard facial features in one time period, and taking the standard facial features as the short-term video features;

a short-term audio feature extraction sub-module used for obtaining, by calculation, rhythm features, tone features, spectrum parameter features and statistics thereof in the audio information in the multiple time periods, and taking the rhythm features, the tone features, the spectrum parameter features and the statistics thereof as the short-term video features; and a short-term text feature extraction sub-module used for obtaining, by calculation, word vectors and statistics thereof in the text information in the multiple time periods, and taking the word vectors and the statistics thereof as the short-term text features.

Optionally, the long-term feature extraction module comprises:

a long-term video feature extraction sub-module used for extracting all short-term video features in each dialogue in the to-be-detected sample, and calculating all the short-term video features in each dialogue in the to-be-detected sample by a self-attention mechanism to obtain the long-term video features of each dialogue in the to-be-detected sample;

a long-term audio feature extraction sub-module used for extracting all short-term audio features in each dialogue in the to-be-detected sample, and calculating all the short-term audio features in each dialogue in the to-be-detected sample by the self-attention mechanism to obtain the long-term audio features of each dialogue in the to-be-detected sample; and a long-term text feature extraction sub-module used for extracting all short-term text features in each dialogue in the to-be-detected sample, and calculating all the short-term text features in each dialogue in the to-be-detected sample by the self-attention mechanism to obtain the long-term text features of each dialogue in the to-be-detected sample.

Optionally, the multi-modal feature integration module comprises:

a feature stitching sub-module used for stitching the long-term video features, the long-term audio features and the long-term text features to obtain multi-modal stitched features; and a multi-modal feature calculation sub-module used for calculating an attention weight of each modality, and integrating the multi-modal stitched features according to the attention weight to obtain the multi-modal feature of each dialogue in the to-be-detected sample, wherein each modality is a video, an audio or a text.

Optionally, the interactive modeling module comprises:

a node representation sub-module used for taking the multi-modal feature of each dialogue as a feature representation of each sentence node in the graph neural network, and taking speaker information corresponding to each dialogue as a feature representation of each speaker in the graph neural network;

a sequential relationship establishing sub-module used for connecting each sentence node in the graph neural network and a neighborhood sentence of the sentence node by means of an edge, and establishing a sequential relationship model of all sentences in the to-be-detected sample to obtain a sequential relationship of the dialogues in the to-be-detected sample, wherein the edges for connecting the sentences nodes include forward edges and backward edges, a time sequence of a node where each forward edge starts is earlier, a time sequence of a node to which each forward edge points is later, a time sequence of a node where each backward edge starts is earlier, and a time sequence of a node to which each backward edge points is later;

a character relationship establishing sub-module used for connecting each sentence node in the graph neutral network and a speaker node corresponding to the sentence node by means of an edge, and establishing a speaker information model of each dialogue in the to-be-detected sample to obtain a relationship between each dialogue in the to-be-detected sample and the corresponding speaker; and an interactive integration sub-module used for integrating the multi-modal feature of each dialogue, the sequential relationship, and the relationship between each dialogue and the corresponding speaker to obtain the multi-modal feature integrated with the interactive information.

Optionally, the long-term video feature extraction sub-module comprises:

a feature mapping sub-module used for assigning the short-term video features in each dialogue in the to-be-detected sample to three variables, performing m times of linear mapping on the three variables, and recording three variables obtained after each time of mapping from the first time of mapping to the mth times of mapping;

a first short-term video feature calculation sub-module used for calculating attention weights of the three variables obtained after each time of mapping, and calculating a weight sum according to the attention weights obtained by calculation to obtain a short-term video feature after each time of mapping;

a second short-term video feature calculation sub-module used for sequentially stitching the short-term video features obtained after each time of mapping to obtain short-term video features integrated with sequential information; and a long-term video feature calculation sub-module used for calculating attention weights of the short-term video features integrated with the sequential information, and calculating a weight sum of the short-term video features integrated with the sequential information according to the attention weights obtained by calculation to obtain the long-term video feature of each dialogue in the to-be-detected sample, wherein the long-term video features and the long-term text features are calculated in a same way as the long-term video features.

In a third aspect, the embodiments of the application provide a computer-readable storage medium, having a computer program stored therein, wherein when the computer program is executed by a processor, the steps of the method according to the first aspect is performed In a fourth aspect, the embodiments of the application provide an electronic device, comprising a memory, a processor, and a computer program stored in the memory and capable of running on the processor, wherein when the processor executes the computer program, the steps of the method according to the first aspect is performed.

According to the automatic lie detection method provided by the application, the video, the audio and the text in the to-be-detected sample are segmented in seconds to obtain the short-term video information, the short-term audio information and the short-term text information; multiple short-term video features, short-term audio features and short-term text features are extracted from the multiple pieces of short-term video information, short-term audio information and short-term text information; the multiple short-term video features are aggregated into a sentence-level long-term video feature, the multiple short-term audio features are aggregated into a sentence-level long-term audio feature, and the multiple short-term text features are aggregated into a sentence-level long-term text feature; the long-term video feature, the long-term audio feature and the long-term text feature are integrated into a multi-modal feature by a self-attention mechanism, and the multi-modal feature and character information features are input to the graph neural network to obtain the multi-modal feature integrated with interactive information, wherein the character information features are extracted by the pre-trained character information recognition network; and the lie level of each dialogue is predicted according to the multi-modal feature integrated with the interactive information. According to the method, the video features, audio features and text features are integrated into the multi-modal feature by the self-attention mechanism, features of three modalities are considered in combination, sequential information of the dialogues and information of each sentence and the corresponding speaker are modeled by the graph neural network, and the multi-modal feature and the interactive information are considered in combination, so that the accuracy of lie detection is improved.

BRIEF DESCRIPTION OF THE DRAWINGS

To more clearly explain the technical solutions of the embodiments of the application, drawings used for describing the embodiments of the application will be briefly introduced below. Obviously, the drawings in the following description merely illustrate some embodiments of the application, and those ordinarily skilled in the art may obtain other drawings according to the following ones without creative labor.

DETAILED DESCRIPTION OF THE EMBODIMENTS

The technical solutions of the embodiments of the application will be clearly and comprehensively described below in conjunction with the accompanying drawings of the embodiments. Obviously, the embodiments in the following description are merely illustrative ones, and are not all possible ones of the application. All other embodiments obtained by those ordinarily skilled in the art based on the following ones without creative labor should also fall within the protection scope of the application.

Figure 1:
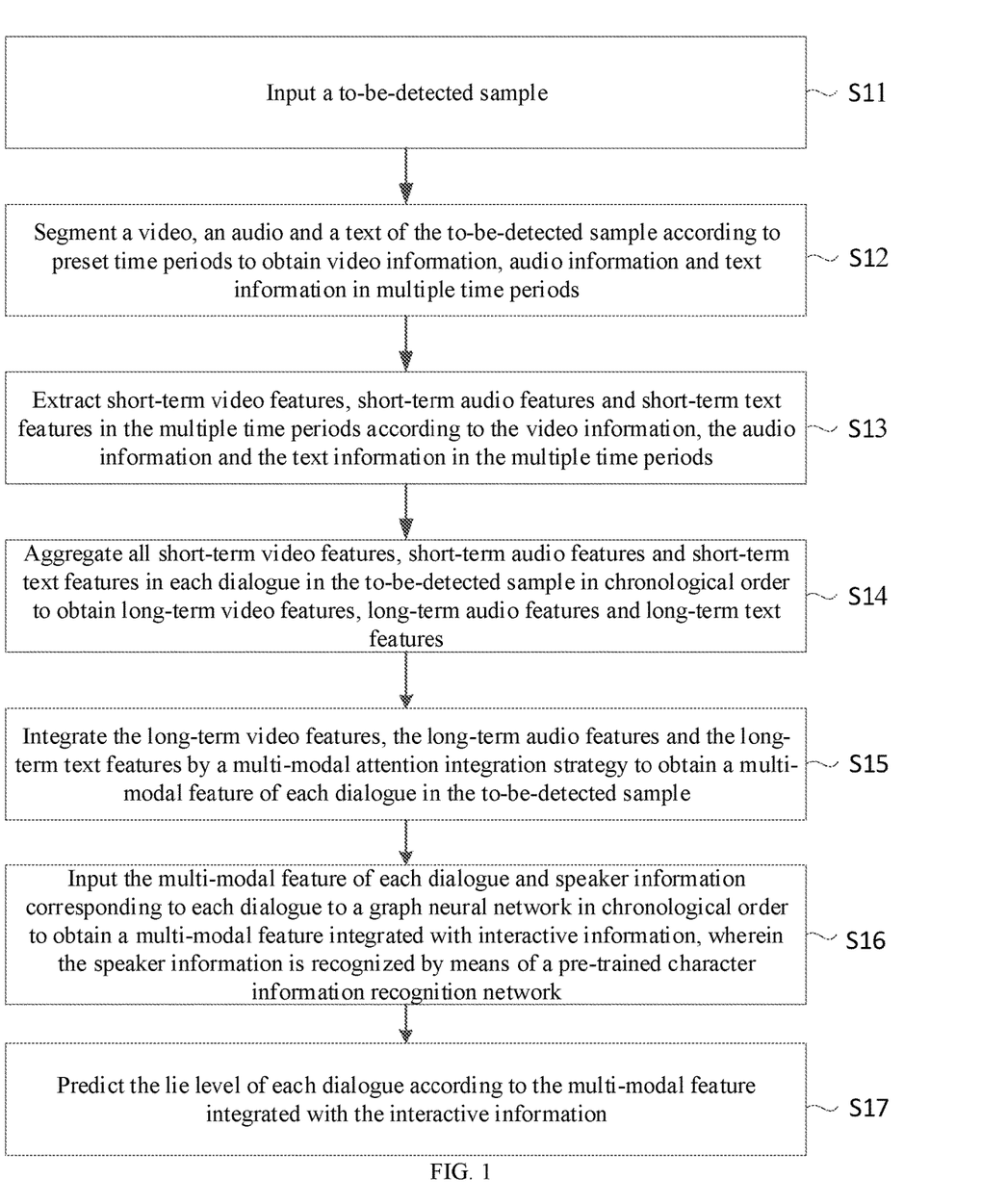
FIG. 1 is a flow diagram of an automatic lie detection method for interactive scenarios according to one embodiment of the application.

Refer to FIG. 1 which is a flow diagram of an automatic lie detection method for interactive scenarios according to one embodiment of the application. As shown in FIG. 1, the method comprises the following steps:

S11: inputting a to-be-detected sample.

In this embodiment, the to-be-tested sample may be a dialogue video including facial expressions and dialogue speeches of speakers, and this embodiment has no limitation in this aspect.

S12: segmenting a video, an audio and a text of the to-be-detected sample according to preset time periods to obtain video information, audio information and text information in multiple time periods.

In this embodiment, images in the to-be-tested samples are a video, speeches in the to-be-detected sample are an audio, and contents of each dialogue in the to-be-detected sample are a text. By segmenting the video, audio and text into short clips, features of each dialogue can be extracted more effectively, which is conducive to improving the accuracy of lie detection.

In this embodiment, segmenting a video, an audio and a text of the to-be-detected sample according to preset time periods to obtain video information, audio information and text information in multiple time periods comprises the following specific steps:

S12-1: segmenting the video of the to-be-detected sample in seconds, taking all image frames, appearing within one second, in the to-be-detected sample as video information in one time period, and normalizing all the image frames in the video information to obtain images of a first preset size.

In this embodiment, feature changes of facial expressions of a speaker can be seen from the video; the video is segmented in seconds, all image frames within one second are taken as video information in one time period, and the image frames should not be overlapped, that is, the time periods should not be overlapped. For example, if the to-be-detected sample lasts for 60 seconds and the frame rate of the to-be-detected sample is 25 frames per second, every 25 frames of images are taken as video information in one time period, that is, 25 frames of images within 0-1 second are taken as video information in a first time period, 25 frames of images within 1-2 second are taken as video information in a second time period, . . . , and 25 frames of images within 59-60 second are taken as video information in a 60th time period.

In this embodiment, all the image frames in the video are normalized to facilitate further processing of the images. For example, all the image frames may be normalized to a size of 300*300.

S12-2: segmenting the audio of the to-be-detected sample in seconds, and taking all audio sampling points, appearing within one second, in the to-be-detected sample as audio information in one time period.

In this embodiment, the sounds, tone and speed of the speaker may be extracted from the audio information in the to-be-detected sample. All audio sampling points appearing within one second are taken as audio information in one time period, and the audio sampling points should not be overlapped, that is, the time periods should not be overlapped. For example, if the to-be-detected sample lasts for 60 seconds and the audio sampling rate of the to-be-detected sample is 16,000 sampling points per second, 16,000 sampling points within 0-1 second are taken as audio information in a first time period, 16,000 sampling points within 1-2 second are taken as audio information in a second time period, . . . , and 16,000 sampling points within 59-60 second are taken as audio information in a 60th time period.

S12-3: segmenting the text of the to-be-detected sample in seconds, and taking words, spoken by a speaker within one second, in the to-be-detected sample as text information in one time period.

In this embodiment, the text in the to-be-detected sample is the contents spoken by the speaker in the sample, and lie detection will be facilitated by combining the words used by the speaker and the context; and all words appearing within one second are taken as text information in one time period, and the words should not be overlapped, that is, the time periods should not be overlapped. For example, if the to-be-detected sample lasts for 60 seconds, words appearing within 0-1 second are taken as text information in a first time period, words appearing within 1-2 second are taken as text information in a second time period, . . . , and words appearing within 59-60 seconds are taken as text information in a 60th time period.

S13: extracting short-term video features, short-term audio features and short-term text features in the multiple time periods according to the video information, the audio information and the text information in the multiple time periods.

In this embodiment, the short-term video features, the short-term audio features and the short-term text features are essentially vectors including the short-term video features, the short-term audio features and the short-term text features.

In this embodiment, extracting short-term video features, short-term audio features and short-term text features in the multiple time periods according to the video information, the audio information and the text information in the multiple time periods comprises the following specific steps:

S13-1: extracting face region images from the short-term video information in the multiple time periods.

In this embodiment, a neural network processes received short-term video information to extract the face region images, from which facial expressions of the speaker are extracted.

S13-2: correcting and normalizing the face region images to obtain standard facial images of a second preset size.

In this embodiment, the face region images are corrected to rectify the face in the face region images to a normal angle, which is beneficial to the extraction of facial information. After the face is rectified to the normal angle, the face region images are normalized to obtain standard facial images of a second preset size, such as 100*100 standard facial images.

S13-3: extracting, by a pre-trained facial expression recognition network, hidden-layer feature representations from the standard facial images to obtain standard facial features.

In this embodiment, the facial expression recognition network is trained by means of collected images marked with expressions, and hidden-layer feature representations are extracted from the standard facial images, that is, each pixel of the facial images is analyzed by a hidden layer after the facial images are input to the neural network, such that facial expression features of the speaker are obtained.

S13-4: performing feature statistics on the standard facial features to obtain standard facial features in one time period, and taking the standard facial features as the short-term video features.

In this embodiment, a facial image exits in each frame in one time period, and all the facial features in one time period are counted to be taken as the short-term video features. The short-term video features may include the slanting angle of mouth corners of the speaker, the pupil size of the speaker, and whether the speaker frowns.

S13-5: obtaining, by calculation, rhythm features, tone features, spectrum parameter features and statistics thereof in the audio information in the multiple time periods, and taking the rhythm features, the tone features, the spectrum parameter features and the statistics thereof as the short-term video features.

In this embodiment, the rhythm features include the pitch, duration and intensity of sounds, the tone features vary according to different speakers, the spectrum parameter features are frequency spectra formed by vocal printers of speakers, and different speakers have different spectrum parameters because their sound tracks are in different shapes. By calculating all the sampling points in each time period, the rhythm features, tone features and spectrum parameter features in the audio information can be obtained. The statistics is a variable for analyzing and checking these data and effectively reflects the audio features.

S13-6: obtaining, by calculation, word vectors and statistics thereof in the text information in the multiple time periods, and taking the vectors and the statistics thereof as the short-term text features.

In this embodiment, word vectors in the short-term text information in each time period are calculated, and the short-term text features are obtained according to the word vectors and the statistics of the word vectors.

S14: aggregating all short-term video features, short-term audio features and short-term text features in each dialogue in the to-be-detected sample in chronological order to obtain long-term video features, long-term audio features and long-term text features.

In this embodiment, the long-term video features, the long-term audio features and the long-term text features are obtained by aggregating the short-term video features, the short-term audio features and the short-term text features, respectively, and the long-term features are features of each sentence in the to-be-detected sample.

In this embodiment, aggregating all short-term video features, short-term audio features and short-term text features in each dialogue in the to-be-detected sample in chronological order to obtain long-term video features, long-term audio features and long-term text features comprises the following specific steps:

S14-1: extracting all short-term video features in each dialogue in the to-be-detected sample, and calculating all the short-term video features in each dialogue in the to-be-detected sample by a self-attention mechanism to obtain the long-term video features of each dialogue in the to-be-detected sample;

In this embodiment, the self-attention mechanism is an improvement on an attention mechanism, and compared with the attention mechanism, the self-attention mechanism reduces the dependence on external information and is better at capturing data or internal correlations of features. Calculating all the short-term video features in each dialogue in the to-be-detected sample by a self-attention mechanism to obtain the long-term video features of each dialogue in the to-be-detected sample comprises the following specific steps:

S14-1-1: assigning the short-term video features in each dialogue in the to-be-detected sample to three variables, performing m times of linear mapping on the three variables, and recording three variables obtained after each time of mapping from the first time of mapping to the mth times of mapping.

In this embodiment, assume a dialogue $U=[u_1, \ldots, u_N]$ exists in the to-be-detected sample and $u_j$ (j=1, . . . , N) is the jth sentence in the dialogue, short-term features of an audio modality or a text modality are extracted from $u_j$ and are marked as $S_j$, $S_j$ is assigned to three variables Q, K and V, and m times of linear mapping are performed on each variable to obtain:

$$Q_i = QW_i^Q (i=1,\ldots,m) \quad (1)$$

$$K_i = KW_i^K (i=1,\ldots,m) \quad (2)$$

$$V_i = VW_i^V (i=1,\ldots,m) \quad (3)$$

Wherein, $W_i^Q$, $W_i^K$, $W_i^V$ are mapping parameters of Q, K and V respectively, and $Q_i$, $K_i$, $V_i$ are values obtained after m times of linear mapping.

S14-1-2: calculating attention weights of the three variables obtained after each time of mapping, and calculating a weight sum according to the attention weights obtained by calculation to obtain a short-term video feature after each time of mapping.

In this embodiment, $Q_i$, $K_i$, $V_i$ are input to an attention module, and an output of the attention module is marked as $head_i$:

$$head_i = \text{softmax}(Q_i K_i^T) \quad (4)$$

Wherein, $\text{softmax}(Q_i K_i^T)$ is the calculated attention weight and is used for calculating the weight sum of $V_i$, and $head_i$ is the short-term video feature obtained after the mth times of mapping.

S14-1-3: sequentially stitching the short-term video features obtained after each time of mapping to obtain short-term video features integrated with sequential information In this embodiment, $head^i$ (i=1, ..., m) are stitched to obtain the short-term video features Z integrated with the sequential information:

$$Z = \text{Concat}(head_1,\ldots,head_m) \quad (5)$$

Wherein, Z is the short-term video features Z integrated with the sequential information, and contact ( ) refers to stitching of vectors.

S14-1-4: calculating attention weights of the short-term video features integrated with the sequential information, and calculating a weight sum of the short-term video features integrated with the sequential information according to the attention weights obtained by calculation to obtain the long-term video feature of each dialogue in the to-be-detected sample, wherein the long-term video features and the long-term text features are calculated in the same way as the long-term video features.

The short-term features Z are input to a paragraph-level attention module to obtain long-term features G. The paragraph-level attention module is able to focus on key paragraph information to better distinguish lie features:

$$A = \text{softmax}(ZW_z) \quad (6)$$

$$G = AZ \quad (7)$$

Wherein, softmax( ) is a calculation function, $W_z$ is a trainable parameter, A is an attention weight corresponding to the feature of each paragraph, G is a result obtained after weight integration of the short-term features Z based on an attention A, that is, the long-term video feature of each dialogue.

S14-2: extracting all short-term audio features in each dialogue in the to-be-detected sample, and calculating all the short-term audio features in each dialogue in the to-be-detected sample by the self-attention mechanism to obtain the long-term audio features of each dialogue in the to-be-detected sample.

In this embodiment, the long-term audio features may also be obtained by calculation according to S14-1-1 to S14-1-4, and details will no longer be given here.

S14-3: extracting all short-term text features in each dialogue in the to-be-detected sample, and calculating all the short-term text features in each dialogue in the to-be-detected sample by the self-attention mechanism to obtain the long-term text features of each dialogue in the to-be-detected sample.

In this embodiment, the long-term text features may also be obtained by calculation according to S14-1-1 to S14-1-4, and details will no longer be given here.

S15: integrating the long-term video features, the long-term audio features and the long-term text features by a multi-modal attention integration strategy to obtain a multi-modal feature of each dialogue in the to-be-detected sample.

In this embodiment, lies may be detected according to video features, audio feature and text features by the multi-modal attention fusion strategy. Integrating the long-term video features, the long-term audio features and the long-term text features by a multi-modal attention integration strategy to obtain a multi-modal feature of each dialogue in the to-be-detected sample comprises the following specific steps:

S15-1: stitching the long-term video features, the long-term audio features and the long-term text features to obtain multi-modal stitched features.

In this embodiment, the long-term features of the three modalities are stitched to obtain the multi-modal features, wherein feature vectors of the three modalities in each dialogue are directly stitched to obtain the multi-modal stitched features. Assume $G_A$ is the long-term audio feature, $G_L$ is the long-term text feature and $G_V$ is the long-term facial feature, the multi-modal feature is as follows:

$$G_{cat} = \text{Concat}(G_A, G_L, G_V) \quad (8)$$

Wherein, $G_{cat}$ is a vector obtained after stitching, and contact( ) refers to stitching of three vectors.

S15-2: calculating an attention weight of each modality, and integrating the multi-modal stitched features according to the attention weight to obtain the multi-modal feature of each dialogue in the to-be-detected sample, wherein each modality is a video, an audio or a text.

In this embodiment, the attention weight of each modality is calculated, and the multi-modal features are obtained according to the attention weight as follows:

$$P_F = \tan h(W_F G_{cat}) \quad (9)$$

$$A_F = \text{softmax}(w_F^T P_F) \quad (10)$$

$$F = G_{cat} A_F \quad (11)$$

Wherein, $W_F$ and $w_F$ are trainable parameters, and $A_F$ is the attention weight of each modality; and $P_F$ is a median, and F is the multi-modal feature.

In this embodiment, the long-term features of the three modalities are integrated into the multi-modal features by the attention mechanism, and when receiving the multi-modal feature of each sentence, the neural network will emphatically analyze a part with a high weight. For example, when the speaker in the to-be-detected sample speaks a sentence, the expression and words of the speaker are normal, but the tone of the speaker is suddenly increased or decreased, and in this case, the neural network will emphatically analyze a part, representing the tone of the speaker, of the multi-modal feature.

S16: inputting the multi-modal feature of each dialogue and speaker information corresponding to each dialogue to a graph neural network in chronological order to obtain a multi-modal feature integrated with interactive information, wherein the speaker information is recognized by means of a pre-trained character information recognition network.

In this embodiment, pre-marked character images and corresponding character information are taken as a training set to train a character information recognition network to obtain the trained character information recognition network, and when receiving character images, the character information recognition network is able to recognize character feature information, such as identity information.

In this embodiment, inputting the multi-modal feature of each dialogue and speaker information corresponding to each dialogue to a graph neural network in chronological order to obtain a multi-modal feature integrated with interactive information comprises the following specific steps:

S16-1: taking the multi-modal feature of each dialogue as a feature representation of each sentence node in the graph neural network, and taking the speaker information corresponding to each dialogue as a feature representation of each speaker in the graph neural network.

In this embodiment, the graph neural network is a graph convolutional network and consists of multiple nodes and edges. Assume the dialogue is $U=[u_1, \ldots, u_N]$ and $u_j$ ($j=1, \ldots, N$) is the jth sentence in the dialogue, the multi-modal feature representation of each sentence obtained after the sentence is processed by a multi-modal feature integration module is $f_j$ ($j=1, \ldots, N$). The whole dialogue U is expressed as the graph neural network which comprises two types of nodes: sentence nodes and speaker nodes. $f_j$ is taken as a feature representation of each sentence node, and figure features recognized by the pre-trained figure information recognition network, such as x-vector, are taken as the speaker nodes, wherein the x-vector is a neural network and has a good character information recognition effect.

S16-2: connecting each sentence node in the graph neural network and a neighborhood sentence of the sentence node by means of an edge, and establishing a sequential relationship model of all sentences in the to-be-detected sample to obtain a sequential relationship of the dialogues in the to-be-detected sample, wherein the edges for connecting the sentences nodes include forward edges and backward edges, a time sequence of a node where each forward edge starts is earlier, a time sequence of a node to which each forward edge points is later, a time sequence of a node where each backward edge starts is earlier, and a time sequence of a node to which each backward edge points is later.

S16-3: connecting each sentence node in the graph neutral network and a speaker node corresponding to the sentence node by means of an edge, and establishing a speaker information model of each dialogue in the to-be-detected sample to obtain a relationship between each dialogue in the to-be-detected sample and the corresponding speaker.

S16-4: integrating the multi-modal feature of each dialogue, the sequential relationship, and the relationship between each dialogue and the corresponding speaker to obtain the multi-modal feature integrated with the interactive information.

In this embodiment, after the multi-modal features are obtained by the graph neural network, feature representations integrated with interactive information are acquired. For a single-layer graph neural network:

$$h_i^{(1)} = \text{Re}LU\left(\sum_{r \in R} \sum_{j \in N_i^r} \frac{w_{ij}}{|N_i^r|} W_r^{(1)} h_j^{(0)}\right) \quad (12)$$

Wherein, Re LU ( ) is a rectified linear unit, R is an edge set, $N_i^r$ is a set of nodes connected to a node i under a relation r, and $|N_i^r|$ is the number of elements included in the set $N_i^r$; $w_{ij}$ is the weight of an edge between the node i and the node j, $W_r^{(1)}$ is a weight parameter corresponding to the relation r, and $h_j^{(0)}$ is an initial feature of the node j; for the sentence nodes, $h_j^{(0)}$ is $f_j$; for the speaker nodes, $h_j^{(0)}$ is figure feature vectors; and $h_i^1$ is the multi-modal feature integrated with interactive information output by the node i in the single-layer graph neural network.

For a multi-layer graph neural network:

$$h_i^{(l)} = \text{Re}LU\left(\sum_{r \in R} \sum_{j \in N_i^r} \frac{w_{ij}}{|N_i^r|} W_r^{(l)} h_j^{(l-1)}\right) \quad (13)$$

Assume the network includes L layers, an output of the final node i is $h_i^{(L)}$, and $h_i^1$ is the multi-modal feature integrated with interactive information output by the node i of the L-layer network.

In this embodiment, the multi-modal features are integrated with the sequential information and the interactive information, and the influence of the lie state at a previous moment on the lie state at the current moment can be considered by means of the sequential information, for example, if the probability that words spoken by the speaker at the previous moment are a lie, it is more likely that the words spoken by the speaker at the current moment is a lie. The interactive information also has an influence on the lie state of the speaker, for example, an interrogee may change the lie state under the influence of an interrogator during an interrogation.

S17: predicting the lie level of each dialogue according to the multi-modal feature integrated with the interactive information.

In this embodiment, the graph neural network outputs the multi-modal features integrated with the interactive information, and the lie level of the dialogue is predicted according to the multi-modal feature of each sentence of the dialogue. For example, the lie level of each sentence of the dialogue may be calculated by a single-layer perceptron as follows:

$$P_i = \text{softmax}(h_i W_l) \quad (14)$$

Wherein, soft max ( ) is a calculation function, and $W_l$ is a parameter of the single-layer perceptron; $P_i$ is a prediction result of the lie level, which indicates the probability of the sentence being true and the probability of the sentence being a lie, and $h_i$ is the multi-modal feature integrated with the interactive information output by the node i.

By adoption of Si11-S17 in this embodiment, the to-be-detected sample is segmented first to obtain multiple pieces of short-term video information, short-term audio information and short-term text information, short-term video features, short-term audio features and short-term text features are extracted from the multiple pieces of short-term video information, short-term audio information and short-term text information, all the short-term video features, short-term audio features and short-term text features of each dialogue are integrated by the self-attention mechanism to obtain a long-term video feature, a long-term audio feature and a long-term text feature of each dialogue, the long-term video feature, the long-term audio feature and the long-term text feature of each dialogue are integrated by the multi-modal attention integration strategy to obtain a multi-modal feature of each dialogue, the multi-modal feature of each dialogue and corresponding character features are input to the neural network to obtain a multi-modal feature integrated with interactive information, and the lie level of each dialogue is predicted according to the multi-modal feature integrated with the interactive information. The multi-modal information and interactive information are combined for lie detection, so that the accuracy of lie detection is greatly improved.

Figure 2:
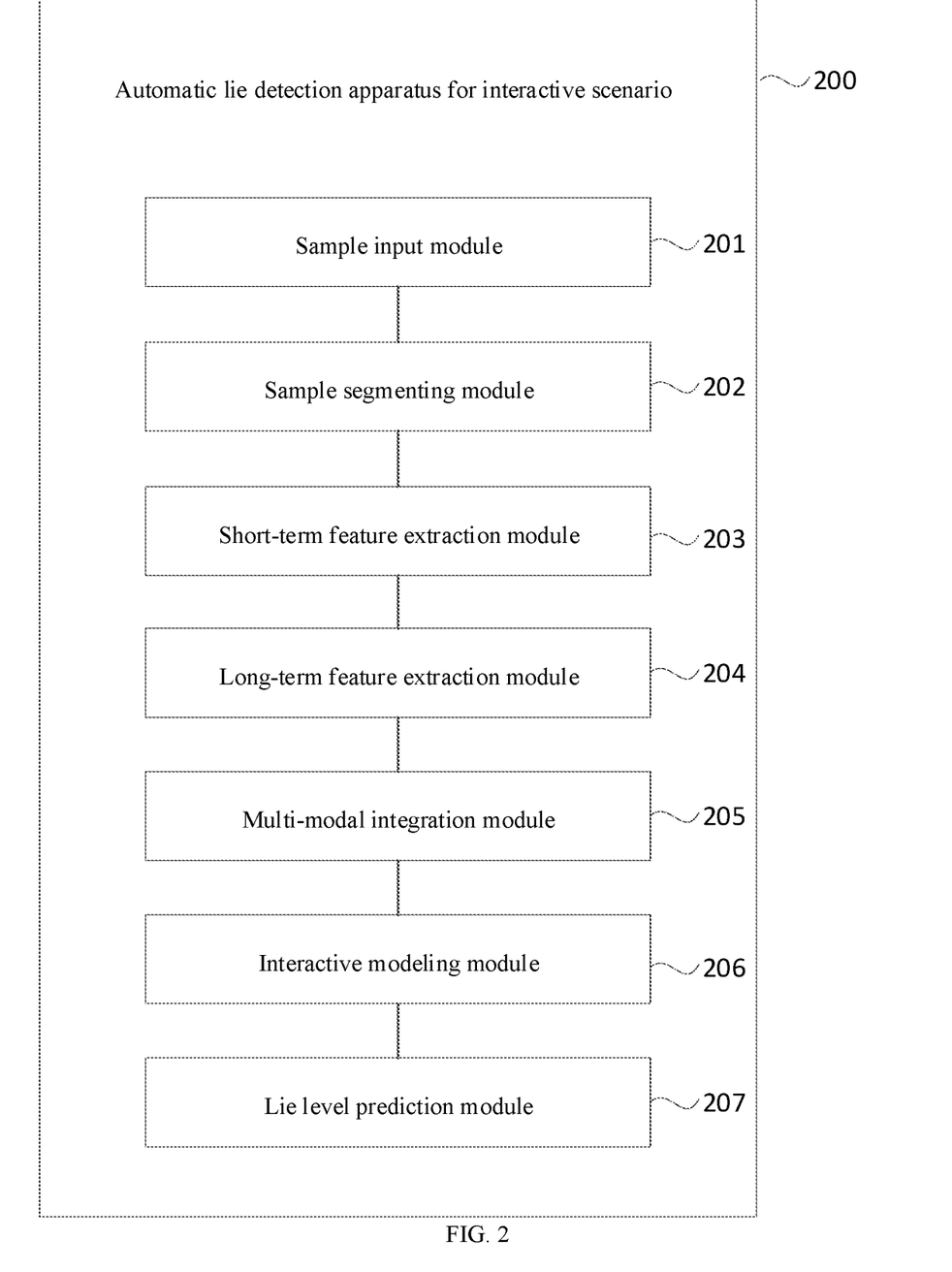
FIG. 2 is a schematic diagram of an automatic lie detection apparatus for interactive scenarios according to one embodiment of the application.

Based on the same inventive concept, one embodiment of the application provides an automatic lie detection apparatus for interactive scenarios. Refer to FIG. 2 which is a schematic diagram of the automatic lie detection apparatus 200 for interactive scenarios according to one embodiment of the application. As shown in FIG. 2, the apparatus comprises:

A sample input module 201 used for inputting a to-be-detected sample;

A sample segmenting module 202 used for segmenting a video, an audio and a text of the to-be-detected sample according to preset time periods to obtain video information, audio information and text information in multiple time periods;

A short-term feature extraction module 203 used for extracting short-term video features, short-term audio features and short-term text features in the multiple time periods according to the video information, the audio information and the text information in the multiple time periods;

A long-term feature extraction module 204 used for aggregating all short-term video features, short-term audio features and short-term text features in each dialogue in the to-be-detected sample in chronological order to obtain long-term video features, long-term audio features and long-term text features;

A multi-modal integration module 205 used for integrating the long-term video features, the long-term audio features and the long-term text features by a multi-modal attention integration strategy to obtain a multi-modal feature of each dialogue in the to-be-detected sample;

An interactive modeling module 205 used for inputting the multi-modal feature of each dialogue and speaker information corresponding to each dialogue to a graph neural network in chronological order to obtain a multi-modal feature integrated with interactive information, wherein the speaker information is recognized by means of a pre-trained character information recognition network; and A lie level prediction module 207 used for predicting the lie level of each dialogue according to the multi-modal feature integrated with the interactive information.

Optionally, the sample segmenting module comprises:

A video segmenting sub-module used for segmenting the video of the to-be-detected sample in seconds, taking all image frames, appearing within one second, in the to-be-detected sample as video information in one time period, and normalizing all the image frames in the video information to obtain images of a first preset size;

An audio segmenting sub-module used for segmenting the audio of the to-be-detected sample in seconds, and taking all audio sampling points, appearing within one second, in the to-be-detected sample as audio information in one time period; and A text segmenting sub-module used for segmenting the text of the to-be-detected sample in seconds, and taking words, spoken by a speaker within one second, in the to-be-detected sample as text information in one time period.

Optionally, the short-term feature extraction module comprises:

A first image extraction sub-module used for extracting face region images from the short-term video information in the multiple time periods;

A first image processing sub-module used for correcting and normalizing the face region images to obtain standard facial images of a second preset size;

A facial expression recognition sub-module used for extracting, by a pre-trained facial expression recognition, hidden-layer feature representations from the standard facial images to obtain standard facial features;

A short-term video feature extraction sub-module used for performing feature statistics on the standard facial features to obtain standard facial features in one time period, and taking the standard facial features as the short-term video features;

A short-term audio feature extraction sub-module used for obtaining, by calculation, rhythm features, tone features, spectrum parameter features and statistics thereof in the audio information in the multiple time periods, and taking the rhythm features, the tone features, the spectrum parameter features and the statistics thereof as the short-term video features; and A short-term text feature extraction sub-module used for obtaining, by calculation, word vectors and statistics thereof in the text information in the multiple time periods, and taking the word vectors and the statistics thereof as the short-term text features.

Optionally, the long-term feature extraction module comprises:

A long-term video feature extraction sub-module used for extracting all short-term video features in each dialogue in the to-be-detected sample, and calculating all the short-term video features in each dialogue in the to-be-detected sample by a self-attention mechanism to obtain the long-term video features of each dialogue in the to-be-detected sample;

A long-term audio feature extraction sub-module used for extracting all short-term audio features in each dialogue in the to-be-detected sample, and calculating all the short-term audio features in each dialogue in the to-be-detected sample by the self-attention mechanism to obtain the long-term audio features of each dialogue in the to-be-detected sample; and A long-term text feature extraction sub-module used for extracting all short-term text features in each dialogue in the to-be-detected sample, and calculating all the short-term text features in each dialogue in the to-be-detected sample by the self-attention mechanism to obtain the long-term text features of each dialogue in the to-be-detected sample.

Optionally, the multi-modal feature integration module comprises:

A feature stitching sub-module used for stitching the long-term video features, the long-term audio features and the long-term text features to obtain multi-modal stitched features; and A multi-modal feature calculation sub-module used for calculating an attention weight of each modality, and integrating the multi-modal stitched features according to the attention weight to obtain the multi-modal feature of each dialogue in the to-be-detected sample, wherein each modality is a video, an audio or a text.

Optionally, the interactive modeling module comprises:

A node representation sub-module used for taking the multi-modal feature of each dialogue as a feature representation of each sentence node in the graph neural network, and taking speaker information corresponding to each dialogue as a feature representation of each speaker in the graph neural network;

A sequential relationship establishing sub-module used for connecting each sentence node in the graph neural network and a neighborhood sentence of the sentence node by means of an edge, and establishing a sequential relationship model of all sentences in the to-be-detected sample to obtain a sequential relationship of the dialogues in the to-be-detected sample, wherein the edges for connecting the sentences nodes include forward edges and backward edges, a time sequence of a node where each forward edge starts is earlier, a time sequence of a node to which each forward edge points is later, a time sequence of a node where each backward edge starts is earlier, and a time sequence of a node to which each backward edge points is later;

A character relationship establishing sub-module used for connecting each sentence node in the graph neutral network and a speaker node corresponding to the sentence node by means of an edge, and establishing a speaker information model of each dialogue in the to-be-detected sample to obtain a relationship between each dialogue in the to-be-detected sample and the corresponding speaker; and An interactive integration sub-module used for integrating the multi-modal feature of each dialogue, the sequential relationship, and the relationship between each dialogue and the corresponding speaker to obtain the multi-modal feature integrated with the interactive information.

Optionally, the long-term video feature extraction sub-module comprises:

A feature mapping sub-module used for assigning the short-term video features in each dialogue in the to-be-detected sample to three variables, performing m times of linear mapping on the three variables, and recording three variables obtained after each time of mapping from the first time of mapping to the mth times of mapping;

A first short-term video feature calculation sub-module used for calculating attention weights of the three variables obtained after each time of mapping, and calculating a weight sum according to the attention weights obtained by calculation to obtain a short-term video feature after each time of mapping;

A second short-term video feature calculation sub-module used for sequentially stitching the short-term video features obtained after each time of mapping to obtain short-term video features integrated with sequential information; and A long-term video feature calculation sub-module used for calculating attention weights of the short-term video features integrated with the sequential information, and calculating a weight sum of the short-term video features integrated with the sequential information according to the attention weights obtained by calculation to obtain the long-term video feature of each dialogue in the to-be-detected sample, wherein the long-term video features and the long-term text features are calculated in a same way as the long-term video features.

Based on the same inventive concept, another embodiment of the application provides a readable storage medium having a computer program stored therein, wherein when the computer program is executed by a processor, the steps of the automatic lie detection method for interactive scenarios in any one above-mentioned embodiment are performed.

Based on the same inventive concept, another embodiment of the application provide an electronic device, comprising a memory, a processor, and a computer program stored in the memory and capable of running on the processor, wherein when the processor executes the computer program, the steps of the automatic lie detection method for interactive scenarios in any one above-mentioned embodiment are performed.

The embodiment of the apparatus is basically identical with the embodiment of the method, and thus is briefly described, and relevant contents may be understood with reference to the description of the embodiment of the method.

The embodiments in this specification are described progressively, the differences from other embodiments are emphatically stated in each embodiment, and the similarities of these embodiments may be cross-referenced.

Those skilled in the art would appreciate that the embodiments of the application can be provided as a method, an apparatus, or a computer program product. So, the embodiments of the application may be completely hardware embodiments, completely software embodiments, or embodiments combining software and hardware. In addition, the embodiments of the application may be in the form of a computer program product to be implemented on one or more computer-available storage media (including, but not limited to, a disk memory, a CD-ROM, an optical memory, and the like) comprising computer-available program codes.

The embodiments of the application are described with reference to the flow diagram and/or block diagram of the method, terminal device (system) and computer program product provided by the embodiments of the application. It should be understood that each process and/or block in the flow diagram and/or block diagram and the combinations of processes and/or blocks in the flow diagram and/or block diagram can be implemented by computer program instructions.

These computer program instructions can be configured in a general-purpose computer, a special-purpose computer, an embedded processor, or a processor of other programmable data processing terminals to create a machine, so that the instructions can be executed by the computer or the processor of other programmable data processing terminals to create an apparatus for realizing specific functions in one or more processes in the flow diagram and/or in one or more blocks in the block diagram.

These computer program instructions may also be stored in a computer-readable memory that can guide the computer or other program data processing terminals to work in a specific manner, so that the instructions stored in the computer-readable memory can create a product including an instruction device, and the instruction device implements specific functions in one or more processes of the flow diagram and/or one or more blocks in the block diagram.

These computer program instructions may also be loaded on a computer or other programmable data processing terminal devices, so that the computer or other programmable terminal devices can perform a series of operation steps to carry out processing realized by the computer, and the instructions are executed on the computer or other programmable terminal devices to realize specific functions in one or more processes in the flow diagram and/or one or more block diagrams in the block diagram.

Although the preferred embodiments of the application have been described above, those skilled in the art who have known the basic creative concept of the application can make different alterations and modifications to these embodiments. So, the appended claims are intended to include the preferred embodiments and all alterations and modifications made within the scope of the embodiments of the application.

Finally, it should be noted that relational terms such as "first" and "second" in this specification are merely used to distinguish one entity or operation from the other one, and do not definitely indicate or imply that these entities or operations have any actual relations or sequences. In addition, the term "comprise" or "include" or other variations are intended to refer to non-exclusive inclusion, so that a process, method, article or terminal device comprising a series of elements not only comprises these elements listed, but also comprises other elements that are not clearly listed, or inherent elements of the process, method, article or terminal device. Unless otherwise clearly specified, an element defined by the expression "comprise a" shall not exclusive of other identical elements in a process, method, article or terminal device comprising said element.

The automatic lie detection method and apparatus for interactive scenarios, and the device and medium provided by the application are introduced in detail above, specific examples are used in this specification to expound the principle and implementation of the application, and the description of the above embodiments is merely used to assist those skilled in the art in understanding the method and core concept thereof of the application. In addition, those ordinarily skilled in the art can make changes to the specific implementation and application scope based on the concept of the application. So, the contents of the specification should not be construed as limitations of the application.

What is claimed is:

1. An automatic lie detection method for interactive scenarios, comprising:
   inputting a to-be-detected sample;
   segmenting a video, an audio and a text of the to-be-detected sample according to preset time periods to obtain video information, audio information and text information in multiple time periods;
   extracting short-term video features, short-term audio features and short-term text features in the multiple time periods according to the video information, the audio information and the text information in the multiple time periods;
   aggregating the short-term video features, the short-term audio features and the short-term text features in each dialogue in the to-be-detected sample in chronological order to obtain long-term video features, long-term audio features and long-term text features;
   integrating the long-term video features, the long-term audio features and the long-term text features by a multi-modal attention integration strategy to obtain a multi-modal feature of the each dialogue in the to-be-detected sample;
   inputting the multi-modal feature of the each dialogue and speaker information corresponding to the each dialogue to a graph neural network in chronological order to obtain a multi-modal feature integrated with interactive information, wherein the speaker information is recognized by a pre-trained character information recognition network; and
   predicting a lie level of the each dialogue according to the multi-modal feature integrated with the interactive information.

2. The automatic lie detection method according to claim 1, wherein segmenting the video, the audio and the text of the to-be-detected sample according to the preset time periods to obtain the video information, the audio information and the text information in the multiple time periods comprises:
   segmenting the video of the to-be-detected sample in seconds, taking image frames, appearing within one second, in the to-be-detected sample as the video information in one time period, and normalizing the image frames in the video information to obtain images of a first preset size;
   segmenting the audio of the to-be-detected sample in seconds, and taking audio sampling points, appearing within one second, in the to-be-detected sample as the audio information in one time period; and
   segmenting the text of the to-be-detected sample in seconds, and taking words, spoken by a speaker within one second, in the to-be-detected sample as the text information in one time period.

3. The automatic lie detection method according to claim 1, wherein extracting the short-term video features, the short-term audio features and the short-term text features in the multiple time periods according to the video information, the audio information and the text information in the multiple time periods comprises:
   extracting face region images from the short-term video information in the multiple time periods;
   correcting and normalizing the face region images to obtain standard facial images of a second preset size;
   extracting, by a pre-trained facial expression recognition network, hidden-layer feature representations from the standard facial images to obtain standard facial features;
   performing feature statistics on the standard facial features to obtain the standard facial features in one time period, and taking the standard facial features in the one time period as the short-term video features;
   obtaining, by calculation, rhythm features, tone features, spectrum parameter features and statistics of the rhythm features, the tone features and the spectrum parameter features in the audio information in the multiple time periods, and taking the rhythm features, the tone features, the spectrum parameter features and the statistics of the rhythm features, the tone features and the spectrum parameter features as the short-term video features; and
   obtaining, by calculation, word vectors and statistics of the word vectors in the text information in the multiple time periods, and taking the word vectors and the statistics of the word vectors as the short-term text features.

4. The automatic lie detection method according to claim 1, wherein aggregating the short-term video features, the short-term audio features and the short-term text features in the each dialogue in the to-be-detected sample in chronological order to obtain the long-term video features, the long-term audio features and the long-term text features comprises:
   extracting the short-term video features in the each dialogue in the to-be-detected sample, and calculating the short-term video features in the each dialogue in the to-be-detected sample by a self-attention mechanism to obtain the long-term video features of the each dialogue in the to-be-detected sample;
   extracting the short-term audio features in the each dialogue in the to-be-detected sample, and calculating the short-term audio features in the each dialogue in the to-be-detected sample by the self-attention mechanism to obtain the long-term audio features of the each dialogue in the to-be-detected sample; and extracting the short-term text features in the each dialogue in the to-be-detected sample, and calculating the short-term text features in the each dialogue in the to-be-detected sample by the self-attention mechanism to obtain the long-term text features of the each dialogue in the to-be-detected sample.

5. The automatic lie detection method according to claim 4, wherein extracting the short-term video features in the each dialogue in the to-be-detected sample, and calculating the short-term video features in the each dialogue in the to-be-detected sample by the self-attention mechanism to obtain the long-term video features of the each dialogue in the to-be-detected sample comprises:

assigning the short-term video features in the each dialogue in the to-be-detected sample to three variables, performing m times of linear mapping on the three variables, and recording the three variables obtained after each time of mapping from a first time of mapping to an $m^{th}$ times of mapping;

calculating attention weights of the three variables obtained after the each time of mapping, and calculating a weight sum according to the attention weights obtained by calculation to obtain a short-term video feature after the each time of mapping;

sequentially stitching the short-term video features obtained after the each time of mapping to obtain short-term video features integrated with sequential information; and calculating attention weights of the short-term video features integrated with the sequential information, and calculating a weight sum of the short-term video features integrated with the sequential information according to the attention weights obtained by calculation to obtain each long-term video feature of the each dialogue in the to-be-detected sample, wherein the long-term video features and the long-term text features are calculated in a same way as the long-term video features.

6. The automatic lie detection method according to claim 1, wherein integrating the long-term video features, the long-term audio features and the long-term text features by the multi-modal attention integration strategy to obtain the multi-modal feature of the each dialogue in the to-be-detected sample comprises:

stitching the long-term video features, the long-term audio features and the long-term text features to obtain multi-modal stitched features; and calculating an attention weight of each modality, and integrating the multi-modal stitched features according to the attention weight to obtain the multi-modal feature of the each dialogue in the to-be-detected sample, wherein the each modality is a video, an audio or a text.

7. The automatic lie detection method according to claim 1, wherein inputting the multi-modal feature of the each dialogue and the speaker information corresponding to the each dialogue to the graph neural network in chronological order to obtain the multi-modal feature integrated with the interactive information comprises:

taking the multi-modal feature of the each dialogue as a feature representation of each sentence node in the graph neural network, and taking the speaker information corresponding to the each dialogue as a feature representation of each speaker in the graph neural network;

connecting the each sentence node in the graph neural network and a neighborhood sentence of the each sentence node by an edge, and establishing a sequential relationship model of sentences in the to-be-detected sample to obtain a sequential relationship of dialogues in the to-be-detected sample, wherein edges for connecting sentence nodes comprise forward edges and backward edges, a first time sequence of a node where each forward edge starts is earlier, a second time sequence of the node to where the each forward edge points is later, a third time sequence of the node where each backward edge starts is earlier, and a fourth time sequence of the node to where the each backward edge points is later;

connecting the each sentence node in the graph neutral network and a speaker node corresponding to the each sentence node by the edge, and establishing a speaker information model of the each dialogue in the to-be-detected sample to obtain a relationship between the each dialogue in the to-be-detected sample and a corresponding speaker; and integrating the multi-modal feature of the each dialogue, the sequential relationship, and the relationship between the each dialogue and the corresponding speaker to obtain the multi-modal feature integrated with the interactive information.

8. A non-transitory computer-readable storage medium storing a computer program that, when executed by a processor, the steps of the automatic lie detection method according to claim 1 is performed.

9. An electronic device, comprising a memory, a processor, and a computer program stored in the memory and capable of running on the processor, wherein when the processor executes the computer program, the steps of the automatic lie detection method according to claim 1 is performed.

10. An automatic lie detection apparatus for interactive scenarios, comprising:

a sample input module used for inputting a to-be-detected sample;

a sample segmenting module used for segmenting a video, an audio and a text of the to-be-detected sample according to preset time periods to obtain video information, audio information and text information in multiple time periods;

a short-term feature extraction module used for extracting short-term video features, short-term audio features and short-term text features in the multiple time periods according to the video information, the audio information and the text information in the multiple time periods;

a long-term feature extraction module used for aggregating the short-term video features, the short-term audio features and the short-term text features in each dialogue in the to-be-detected sample in chronological order to obtain long-term video features, long-term audio features and long-term text features;

a multi-modal integration module used for integrating the long-term video features, the long-term audio features and the long-term text features by a multi-modal attention integration strategy to obtain a multi-modal feature of the each dialogue in the to-be-detected sample;

an interactive modeling module used for inputting the multi-modal feature of the each dialogue and speaker information corresponding to the each dialogue to a graph neural network in chronological order to obtain a multi-modal feature integrated with interactive information, wherein the speaker information is recognized by a pre-trained character information recognition network; and a lie level prediction module used for predicting a lie level of the each dialogue according to the multi-modal feature integrated with the interactive information.

* * * * *